United States Patent [19]

Liversidge et al.

[11] Patent Number: 5,145,684

[45] Date of Patent: Sep. 8, 1992

[54] SURFACE MODIFIED DRUG NANOPARTICLES

[75] Inventors: Gary G. Liversidge, West Chester; Kenneth C. Cundy, Pottstown, both of Pa.; John F. Bishop, Rochester; David A. Czekai, Honeoye Falls, both of N.Y.

[73] Assignee: Sterling Drug Inc., New York, N.Y.

[21] Appl. No.: 647,105

[22] Filed: Jan. 25, 1991

[51] Int. Cl.[5] ............................................. A61K 9/14
[52] U.S. Cl. .................................. 424/489; 424/495; 424/499
[58] Field of Search ...................... 424/495, 489, 499

[56] References Cited

U.S. PATENT DOCUMENTS

| | | | |
|---|---|---|---|
| 2,671,750 | 3/1954 | Macek | 514/179 |
| 4,107,288 | 8/1978 | Oppenheim | 424/499 |
| 4,540,602 | 9/1985 | Motoyama | 424/495 |
| 4,826,689 | 5/1989 | Violanto | 424/489 |
| 4,851,421 | 7/1989 | Iwasaki et al. | 514/352 |

FOREIGN PATENT DOCUMENTS

| | | |
|---|---|---|
| 411629 | 2/1991 | European Pat. Off. |
| 2282330 | 11/1990 | Japan. |
| 2185397 | 7/1987 | United Kingdom. |
| 2200048 | 7/1988 | United Kingdom. |

OTHER PUBLICATIONS

Lachman et al., "the Theory and Practice of Industrial Pharmacy", Chapter 2, Milling (1986).
Remington's Pharmaceutical Sciences 17th Edition, Chapter 20, Schott, H., "Colloidal Dispersions".

*Primary Examiner*—Thurman K. Page
*Assistant Examiner*—William E. Benston, Jr.
*Attorney, Agent, or Firm*—Arthur H. Rosenstein; William J. Davis

[57] ABSTRACT

Dispersible particles consisting essentially of a crystalline drug substance having a surface modifier adsorbed on the surface thereof in an amount sufficient to maintain an effective average particle size of less than about 400 nm, methods for the preparation of such particles and dispersions containing the particles. Pharmaceutical compositions containing the particles exhibit unexpected bioavailability and are useful in methods of treating mammals.

20 Claims, No Drawings

SURFACE MODIFIED DRUG NANOPARTICLES

FIELD OF THE INVENTION

This invention relates to drug particles, methods for the preparation thereof and dispersions containing the particles. This invention further relates to the use of such particles in pharmaceutical compositions and methods of treating mammals.

BACKGROUND OF THE INVENTION

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 10 mg/ml, tend to be eliminated from the gastrointestinal tract before being absorbed into the circulation. Moreover, poorly water soluble drugs tend to be unsafe for intravenous administration techniques, which are used primarily in conjunction with fully soluble drug substances.

It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. For example, dry milling techniques have been used to reduce particle size and hence influence drug absorption. However, in conventional dry milling, as discussed by Lachman, et al., *The Theory and Practice of Industrial Pharmacy*, Chapter 2, "Milling", p. 45, (1986), the limit of fineness is reached in the region of 100 microns (100,000 nm) when material cakes on the milling chamber. Lachman, et al. note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airjet milling techniques have provided particles ranging in average particle size from as low as about 1 to 50 μm (1,000–50,000 nm).

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptably large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process.

U.S. Pat. No. 4,540,602 (Motoyama et al.) discloses a solid drug pulverized in an aqueous solution of a water-soluble high molecular substance using a wet grinding machine. However, Motoyama et al. teach that as a result of such wet grinding, the drug is formed into finely divided particles ranging from 0.5 μm (500 nm) or less to 5 μm (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible non-solvent for the substance and results in the formation of non-crystalline nanoparticle. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmacodynamically active material. However, the particles comprise a crosslinked matrix of macromolecules having the active material supported on or incorporated into the matrix.

It would be desirable to provide stable dispersible drug particles in the submicron size range which can be readily prepared and which do not appreciably flocculate or agglomerate due to interparticle attractive forces and do not require the presence of a crosslinked matrix. Moreover, it would be highly desirable to provide pharmaceutical compositions having enhanced bioavailability.

SUMMARY OF THE INVENTION

We have discovered stable, dispersible drug nanoparticles and a method for preparing such particles by wet milling in the presence of grinding media in conjunction with a surface modifier. The particles can be formulated into pharmaceutical compositions exhibiting remarkably high bioavailability.

More specifically, in accordance with this invention, there are provided particles consisting essentially of a crystalline drug substance having a surface modifier adsorbed on the surface thereof in an amount sufficient to maintain an effective average particle size of less than about 400 nm.

This invention also provides a stable dispersion consisting essentially of a liquid dispersion medium and the above-described particles dispersed therein.

In another embodiment of the invention, there is provided a method of preparing the above-described particles comprising the steps of dispersing a drug substance in a liquid dispersion medium and applying mechanical means in the presence of grinding media to reduce the particle size of the drug substance to an effective average particle size of less than about 400 nm. The particles can be reduced in size in the presence of a surface modifier. Alternatively, the particles can be contacted with a surface modifier after attrition.

In a particularly valuable and important embodiment of the invention, there is provided a pharmaceutical composition comprising the above-described particles and a pharmaceutically acceptable carrier therefor. Such pharmaceutical composition is useful in a method of treating mammals.

It is an advantageous feature that a wide variety of surface modified drug nanoparticles free of unacceptable contamination can be prepared in accordance with this invention.

It is another advantageous feature of this invention that there is provided a simple and convenient method for preparing drug nanoparticles by wet milling in conjunction with a surface modifier.

Another particularly advantageous feature of this invention is that pharmaceutical compositions are provided exhibiting unexpectedly high bioavailability.

Still another advantageous feature of this invention is that pharmaceutical compositions containing poorly water soluble drug substances are provided which are suitable for intravenous administration techniques.

Other advantageous features will become readily apparent upon reference to the following Description of Preferred Embodiments.

DESCRIPTION OF PREFERRED EMBODIMENTS

This invention is based partly on the discovery that drug particles having an extremely small effective average particle size can be prepared by wet milling in the presence of grinding media in conjunction with a surface modifier, and that such particles are stable and do not appreciably flocculate or agglomerate due to interparticle attractive forces and can be formulated into pharmaceutical compositions exhibiting unexpectedly high bioavailability. While the invention is described herein primarily in connection with its preferred utility, i.e., with respect to nanoparticulate drug substances for use in pharmaceutical compositions, it is also believed to be useful in other applications such as the formulation of particulate cosmetic compositions and the preparation of particulate dispersions for use in image and magnetic recording elements.

The particles of this invention comprise a drug substance. The drug substance exists as a discrete, crystalline phase. The crystalline phase differs from a noncrystalline or amorphous phase which results from precipitation techniques, such as described in EPO 275,796 cited above.

The invention can be practiced with a wide variety of drug substances. The drug substance preferably is present in an essentially pure form. The drug substance must be poorly soluble and dispersible in at least one liquid medium. By "poorly soluble" it is meant that the drug substance has a solubility in the liquid dispersion medium of less than about 10 mg/ml, and preferably of less than about 1 mg/ml. A preferred liquid dispersion medium is water. However, the invention can be practiced with other liquid media in which a drug substance is poorly soluble and dispersible including, for example, aqueous salt solutions, safflower oil and solvents such as ethanol, t-butanol, hexane and glycol. The pH of the aqueous dispersion media can be adjusted by techniques known in the art.

Suitable drug substances can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines. Preferred drug substances include those intended for oral administration and intravenous administration. A description of these classes of drugs and a listing of species within each class can be found in Martindale, The Extra Pharmacopoeia, Twenty-ninth Edition, The Pharmaceutical Press, London, 1989, the disclosure of which is hereby incorporated by reference in its entirety. The drug substances are commercially available and/or can be prepared by techniques known in the art.

Representative illustrative species of drug substances useful in the practice of this invention include:
  17-α-pregno-2,4-dien-20-yno-[2,3-d]-isoxazol-17-ol (Danazol);
  5α,17α,-1'-(methylsulfonyl)-1'H-pregn-20-yno[3,2-c]-pyrazol-17-ol (Steroid A);
  piposulfam;
  piposulfan;
  camptothecin; and
  ethyl-3,5-diacetoamido-2,4,6-triiodobenzoate In particularly preferred embodiments of the invention, the drug substance is a steriod such as danazol or Steroid A or an antiviral agent.

The particles of this invention contain a discrete phase of a drug substance as described above having a surface modifier adsorbed on the surface thereof. Useful surface modifiers are believed to include those which physically adhere to the surface of the drug substance but do not chemically bond to the drug.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986, the disclosure of which is hereby incorporated by reference in its entirety. The surface modifiers are commercially available and/or can be prepared by techniques known in the art.

Particularly preferred surface modifiers include polyvinyl pyrrolidone, Pluronic F68 and F108, which are block copolymers of ethylene oxide and propylene oxide, Tetronic 908, which is a tetrafunctional block copolymer derived from sequential addition of ethylene oxide and propylene oxide to ethylenediamine, dextran, lecithin, Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 80, which is a polyoxyethylene sorbitan fatty acid ester, available from ICI Specialty Chemicals, and Carbowax 3350 and 934, which are polyethylene glycols available from Union Carbide. Surface modifiers which have found to be particularly useful include polyvinylpyrrolidone, Pluronic F-68, and lecithin.

The surface modifier is adsorbed on the surface of the drug substance in an amount sufficient to maintain an effective average particle size of less than about 400 nm. The surface modifier does not chemically react with the drug substance or itself. Furthermore, the individually adsorbed molecules of the surface modifier are essentially free of intermolecular crosslinkages.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a weight average particle size of less than about 400 nm when measured by the above-noted techniques. In preferred embodiments of the invention, the effective average particle size is less than about 250 nm. In some embodiments of the invention, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

The particles of this invention can be prepared in a method comprising the steps of dispersing a drug substance in a liquid dispersion medium and applying mechanical means in the presence of grinding media to reduce the particle size of the drug substance to an effective average particle size of less than about 400 nm. The particles can be reduced in size in the presence of a surface modifier. Alternatively, the particles can be contacted with a surface modifier after attrition.

A general procedure for preparing the particles of this invention is set forth below. The drug substance selected is obtained commercially and/or prepared by techniques known in the art in a conventional coarse form. It is preferred, but not essential, that the particle size of the coarse drug substance selected be less than about 100 μm as determined by sieve analysis. If the coarse particle size of the drug substance is greater than about 100 μm, then it is preferred that the particles of the drug substance be reduced in size to less than 100 μm using a conventional milling method such as airjet or fragmentation milling.

The coarse drug substance selected can then be added to a liquid medium in which it is essentially insoluble to form a premix. The concentration of the drug substance in the liquid medium can vary from about 0.1-60%, and preferably is from 5-30% (w/w). It is preferred, but not essential, that the surface modifier be present in the premix. The concentration of the surface modifier can vary from about 0.1 to about 90%, and preferably is 1-75%, more preferably 20-60%, by weight based on the total combined weight of the drug substance and surface modifier. The apparent viscosity of the premix suspension is preferably less than about 1000 centipoise.

The premix can be used directly by subjecting it to mechanical means to reduce the average particle size in the dispersion to less than 400 nm. It is preferred that the premix be used directly when a ball mill is used for attrition. Alternatively, the drug substance and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the drug substance conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. We have found that zirconium oxide, such as 95% ZrO stabilized with magnesia, zirconium silicate, and glass grinding media provide particles having levels of contamination which are believed to be acceptable for the preparation of pharmaceutical compositions. However, other media, such as stainless steel, titania, alumina, and 95% ZrO stabilized with yttrium, are expected to be useful. Preferred media have a density greater than about 3 g/cm$^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the drug substance. Processing temperatures of less than about 30°-40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of drug substance and surface modifier can vary widely and the optimal amount of the surface modifier can depend, for example, upon the particular drug substance and surface modifier selected, the critical micelle concentration of the surface modifier if it forms micelles, etc. The surface modifier preferably is present in an amount of about 0.1-10 mg per square meter surface area of the drug substance. The surface modifier can be present in an amount of 0.1-90%, preferably 20-60% by weight based on the total weight of the dry particle.

As indicated by the following examples, not every combination of surface modifier and drug substance provides the desired results. Consequently, the applicants have developed a simple screening process whereby compatible surface modifiers and drug substances can be selected which provide stable dispersions of the desired particles. First, coarse particles of a selected drug substance of interest are dispersed in a liquid in which the drug is essentially insoluble, e.g., water at 5% (w/w) and milled for 60 minutes in a DYNO-MILL under the standard milling conditions which are set forth in Example 1 which follows. The milled material is then divided into aliquots and surface modifiers are added at concentrations of 2, 10 and 50% by weight based on the total combined weight of the drug substance and surface modifier. The dispersions are then sonicated (1 minute, 20 kHz) to disperse agglomerates and subjected to particle size analysis by examination under an optical microscope (1000×magnification). If a stable dispersion is observed, then the process for preparing the particular drug substance surface modifier combination can be optimized in accordance with the teachings above. By stable it is meant that the dispersion exhibits no flocculation or particle agglomeration visible to the naked eye at least 15 minutes, and preferably, at least two days or longer after preparation.

The resulting dispersion of this invention is stable and consists of the liquid dispersion medium and the above-described particles. The dispersion of surface modified drug nanoparticles can be spray coated onto sugar spheres or onto a pharmaceutical excipient in a fluid-bed spray coater by techniques well known in the art.

Pharmaceutical compositions according to this invention include the particles described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the drug substance for treatment is effective to obtain a desired therapeutic response for a particular composition and method of administration. The selected dosage level therefore, depends upon the particular drug substance, the desired therapeutic effect, on the route of administration, on the desired duration of treatment and other factors. As noted, it is a particularly advantageous feature that the pharmaceutical compositions of this invention exhibit unexpectedly high bioavailability as illustrated in the examples which follow. Furthermore, it is contemplated that the drug particles of this invention provide more rapid onset of drug action and decreased gastrointestinal irritancy.

It is contemplated that the pharmaceutical compositions of this invention will be particularly useful in oral and parenteral, including intravenous, administration applications. It is expected that poorly water soluble drug substances, which prior to this invention, could not have been administered intravenously, may be administered safely in accordance with this invention. Additionally, drug substances which could not have been administered orally due to poor bioavailability may be effectively administered in accordance with this invention.

While applicants do not wish to be bound by theoretical mechanisms, it is believed that the surface modifier hinders the flocculation and/or agglomeration of the particles by functioning as a mechanical or steric barrier between the particles, minimizing the close, interparticle approach necessary for agglomeration and flocculation. Alternatively, if the surface modifier has ionic groups, stabilization by electrostatic repulsion may result. It was surprising that stable drug particles of such a small effective average particle size and free of unacceptable contamination could be prepared by the method of this invention.

The following examples further illustrate the invention.

EXAMPLE 1

PVP Modified Danazol Particles Prepared in a Ball Mill

A nanoparticulate dispersion of Danazol was prepared using a DYNO-MILL (Model KDL, manufactured by Willy A. Bachoffen AG Maschinenfabrik). The following ingredients were added to a glass vessel and agitated on a roller for 24 hours to dissolve the polyvinylpyrrolidone surface modifier.

Polyvinylpyrrolidone K-15 (made by GAF)—98 g
High purity water—664 g

Subsequently, 327 grams of dry powdered Danazol was added to the above solution and rolled for one week. This step aided in evenly dispersing the Danazol in the surface modifier solution, thereby reducing the treatment time required in the media mill. The Danazol was purchased in a micronized form (average particle size of about 10 microns) from Sterling Drug Inc. The particles had been prepared by a conventional airjet milling technique. This premix was added to a holding vessel and agitated with a conventional propeller mixer at low speed to maintain a homogeneous mixture for the media milling event. The media mill was prepared accordingly for the media milling process. The mill grinding chamber was partially filled with silica glass spheres and the premix was continuously recirculated through the media mill operating at the following conditions:

Grinding vessel: water jacketed stainless steel chamber
Premix flow rate: 250 ml per minute
Available volume of grinding vessel: 555 ml
Media volume: 472 ml of glass beads Media type: size range of 0.5-0.75 mm silica glass beads, unleaded (distributed by Glen Mills, Inc.)
Recirculation time: 240 min
Residence time: 60 min
Impeller speed: 3000 RPM, tangential speed 1952 ft/min (595 m/min)
Grinding vessel coolant: water
Coolant temperature: 50° F. (10° C.)

After recirculating the slurry for 240 minutes, a sample of the dispersion was removed and evaluated for particle size distribution using a sedimentation field flow fractionator (made by DuPont). The particles were determined to have a number average diameter of 77.5 nm and a weight average diameter of 139.6 nm. The particle size of the dispersion ranged in size from 3-320 nm.

EXAMPLE 2

PVP Modified Danazol Particles Prepared in a Ball Mill at Low Solids.

A nanoparticulate dispersion of Danazol was prepared using a ball mill process. A 600 ml cylindrical glass vessel (inside diameter = 3.0 inches (7.6 cm)) was filled approximately halfway with the following grinding media:

Grinding media: zirconium oxide grinding spheres (made by Zircoa, Inc.)
Media size: 0.85-1.18 mm diameter
Media volume: 300 ml The following dry ingredients were added directly to this glass vessel:

Danazol (micronized): 10.8 g
Polyvinylpyrrolidone K-15: 3.24 g
High purity water: 201.96 g Danazol was purchased in the micronized form (average particle size 10 microns) from Sterling Drug Inc. and the polyvinylpyrrolidone was K-15 grade produced by GAF. The cylindrical vessel was rotated horizontally about its axis at 57% of the "critical speed". The critical speed is defined as the rotational speed of the grinding vessel when centrifuging of the grinding media occurs. At this speed the centrifugal force acting on the grinding spheres presses and holds them firmly against the inner wall of the vessel. Conditions that lead to unwanted centrifuging can be computed from simple physical principles.

After 5 days of ball milling, the slurry was separated from the grinding media through a screen and evaluated for particle size with the sedimentation field flow fractionator. The number average particle diameter measured was 84.9 nm and the weight average particle diameter was 169.1 nm. The particles varied in size from 26 to 340 nm. The amount and type of surface modifier was sufficient to provide colloidal stability to agglomeration and to maintain a homogeneous blend of ingredients assuring precise material delivery during subsequent processing steps.

BIOAVAILABILITY TESTING

Bioavailability of Danazol from the nanoparticulate dispersion described above was compared to that from a suspension of unmilled Danazol in fasted male beagle dogs. The unmilled material was prepared as a suspension in the same manner as the dispersion, with the exception of the ball milling process. Both formulations were administered to each of five dogs by oral gavage and plasma obtained via a cannula in the cephalic vein. Plasma Danazol levels were monitored over 24 hours.

The relative bioavailability of Danazol from the nanoparticulate dispersion was 15.9 fold higher than from the Danazol suspension containing Danazol particles having an average particle size of about 10 microns prepared by conventional airjet milling. Comparison of oral plasma levels with dose corrected plasma levels following intravenous administration of Danazol gave a mean absolute bioavailability ($\pm$SEM) of 82.3$\pm$10.1% for the nanoparticulate dispersion and 5.1$\pm$1.9% for the unmilled material.

EXAMPLE 3

PVP Modified Danazol Particles Prepared in a Ball Mill at High Solids

A nanoparticle dispersion of Danazol was prepared using 1 mm diameter glass grinding media (0.85-1.18 mm from Potters Industries). A cylindrical glass vessel having a diameter of 2.75 inches (7.0 cm) with a volume of 400 ml was charged with 212 ml of unleaded glass grinding media. The following ingredients were added to this vessel:

30.4 g of micronized Danazol
9.12 g of Polyvinylpyrrolidone K-15
112.48 g of high purity water This vessel was rotated horizontally on its axis at a controlled rotational speed of 80.4 revolutions per minute (50% of critical speed) for 5 days. The slurry was immediately separated from the grinding media and evaluated for particle size and grinding media attrition using inductively coupled plasma emissions (ICP). The particle size measured with a sedimentation field flow fractionator yielded a number average diameter of 112.7 nm and a weight average diameter of 179.3 nm. The extent of media attrition was measured to establish the purity of the final dispersion using an inductively coupled plasma-atomic emission spectroscopy method. The level of silicon in the final dispersion was less than 10 parts of elemental silicon per million parts of the slurry.

EXAMPLE 4

PVP Modified Danazol Particles

A nanoparticle dispersion of Danazol was prepared for clinical evaluation using a ball milling dispersion method. This dispersion was prepared by milling with glass grinding media. The grinding media used was:

Media type: 0.85-1.18 mm unleaded glass spheres
Media quantity: 6100 ml

The media was added to a 3 gallon porcelain jar. The following ingredients were then added to the jar:

1000 g Danazol (micronized)
300 g Polyvinylpyrrolidone K-15
3700 g high purity water The vessel was rolled 5 days at a rotational speed of 39.5 revolutions per minute (50% critical speed). The liquid slurry was separated from the grinding media with a screen and used to prepare solid oral doses for clinical studies. The dispersion was assessed for particle size using the sedimentation field flow fractionator and was measured to have a number average diameter of 134.9 nm and a weight average diameter of 222.2 nm. The level of contamination from the grinding media was measured (by ICP) to be 36 parts of silicon per million parts of dispersion. Less than 5 ppm of aluminum was detected. X-ray powder diffraction data of the starting powder was compared with the dispersed Danazol and showed the crystal structure morphology of the solid dispersed particles was unchanged by the dispersion process.

EXAMPLE 5

PVP Modified Danazol Particles

A nanoparticulate dispersion of Danazol was prepared using a laboratory media mill and glass grinding media. The media mill was equipped with a 50 ml grinding chamber and the mill was a "Mini" Motormill manufactured by Eiger Machinery Inc.

The media mill was operated at the following process conditions:
Bead charge: 42.5 ml glass spheres
Rotor speed: 5000 RPM (2617 feet per minute (798 m/min) tangential speed)
Grinding media: 0.75-1.0 mm unleaded glass beads (distributed by Glens Mills)

The dispersion formula was prepared by dissolving 27 g of polyvinylpyrrolidone in 183 g of water and agitated in a steel vessel with a 50 mm "Cowles" type blade until the solution was clear and free of undissolved PVP polymer. The rotational speed of the mixer was maintained at 5000 RPM. 90 g of micronized Danazol was slowly added to this blend with the same mixing for 30 min. 200 cc of the premix was added to the holding tank of the mill and recirculated for 5 hours and 51 minutes. The final residence time in the grinding zone was 40 minutes.

The final average particle size was measured and determined to have a number average diameter of 79.9 nm and a weight average diameter of 161.2 nm. The particles varied in size from 30–415 nm. The level of attrition from erosion of the grinding media and grinding vessel were measured (by ICP) to be 170 ppm of iron and 71 ppm silicon. The crystal structure was determined by X-ray diffraction to be unchanged by the dispersion process.

EXAMPLE 6

Lecithin Modified Steroid A Particles

A nanoparticulate dispersion of Steroid A was prepared by ball milling with zirconium oxide grinding beads. The dispersion was prepared in the absence of a surface modifier and a post addition of Lecithin and a sonication step were required to stablize the dispersed phase of Steroid A and prevent agglomeration and rapid sedimentation. A fine particle dispersion of Steroid A was prepared by ball milling the following ingredients:
5 g Steroid A
95 g high purity water Steroid A was in the form of unmilled coarse grains having a particle size of about 100 μm and ranging in size up to about 400 μm.

The following process conditions were used:
Media: 135 ml
Vessel volume: 240 ml
Media type: 0.85-1.18 mm Zirbeads (manufactured by Zircoa Inc.)
Milling time: 4 days
Milling speed: 86 RPM (50% critical speed)

After four days of ball milling the slurry was separated from the grinding media through a screen. One gram of this unstabilized slurry was added to 10 g of an aqueous solution of Lecithin (1% Centrolex "P" by weight in high purity water, Lecithin manufactured by Central Soya Company, Inc.) and mixed by vigorous shaking, followed by a sonication step for 20 seconds using an ultrasonic horn (Model 350 Branson Ultrasonic Power Supply, Horn Diameter=0.5 inch (1.27 cm), Power setting=2). The slurry was sized under a microscope. An Olympus BH-2 optical microscope equipped with phase contrast illumination was used to observe the size and condition of the dispersion.

A drop of the above dilute slurry was placed between a microscope slide and glass cover slip and observed microscopically at high magnification (1,000 times) and compared to the slurry similarly diluted with water only (no surface modifier). The unmodified dispersion exhibited extensive particle agglomeration. The particle size of the unmodified dispersion was more than 10 microns and the unmodified dispersion exhibited no Brownian Motion. Brownian motion is the oscillatory or jiggling motion exhibited by particles in a liquid that fall in the size range of less than about 1 micron. The Lecithin modified particles exhibited rapid Brownian motion. The thus observed dispersion had the characteristics and appearance consistent with a number average particle size of less than 400 nm. Furthermore, it is expected that additional milling would lead to further particle size reduction.

EXAMPLE 7

Alkyl Aryl Polyether Sulfonate Modified Steroid A

Example 6 was repeated except that the Lecithin was replaced with Triton X-200 (manufactured by Rohm and Haas). Similar results were observed.

EXAMPLE 8

Gum Acacia Modified Steroid A

Example 6 was repeated except that the Lecithin was replaced with gum acacia (available from Eastman Kodak Co.) Similar results were observed.

EXAMPLE 9

Sodium Lauryl Sulfate Modified Steroid A

Example 6 was repeated except that the Lecithin was replaced with sodium lauryl sulfate (available as Duponol ME from DuPont, Inc.). Similar results were observed.

EXAMPLE 10

Steroid A Modified with a Dioctylester of Sodium Sulfosuccinic Acid

Example 6 was repeated except that the Lecithin was replaced with Aerosol OT (available from American Cyanamid Chemical Products, Inc.). Similar results were observed.

EXAMPLE 11

Steroid A Modified with a Block Copolymer of Ethylene Oxide and Propylene Oxide Example 6 was repeated except that the Lecithin was replaced with Pluronic F68 (available from BASF Corp.). Similar results were observed.

EXAMPLE 12

Steroid A Modified with a Block Copolymer of Ethylene Oxide and Propylene Oxide A nanoparticulate dispersion of Steroid A was prepared by ball milling with zirconium oxide grinding media for 5 days. 70 cc of grinding media were added to a 115 cc vessel followed by:

2.5 g Steroid A
0.75 g of Pluronic F68
46.75 g high purity water

The resulting mixture was ball milled for 5 days at 50% of the critical rotational speed. The final dispersion was separated from the grinding media and microscopically evaluated for particle size as in Example 6. The dispersion exhibited rapid Brownian Motion and no particles were larger than 1 micron. Most particles were less than 400 nm.

EXAMPLE 13

Lecithin Modified Steroid A Particles

Example 12 was repeated except that the Pluronic F68 was replaced with Centrolex P. No particles larger than 1 micron were observed microscopically and most were less than 400 nm.

EXAMPLE 14

Steroid A Particles Modified with a Block Copolymer of Ethylene Oxide and Propylene Oxide A nanoparticulate dispersion of Steroid A was prepared by a ball milling process. The following ingredients were added to a cylindrical 0.95 l vessel. The vessel was filled approximately halfway with the following grinding media:

Grinding media: 0.85-1.18 mm diameter zirconium oxide spheres (made by Zircoa)

The following dispersion ingredients were added directly to the glass vessel:

18 g Steroid A
4.5 g Pluronic F68 (purchased from BASF Corp.)
336.6 g high purity water Steroid A was purchased from Sterling Drug Inc. in the form of unmilled tabular crystals having an average particle size of approximately 100 μm.

The vessel was rotated concentrically on its axis at 50% critical speed for 5 days. After this time 4.45 g of Pluronic F68 was added to the slurry and rolled for 5 more days at the same conditions. The slurry was then discharged and separated from the grinding media and evaluated for particle size using the sedimentation field flow fractionator. The number average particle size measured was 204.6 nm and the weight average particle size was 310.6 nm. The particle size distribution ranged from approximately 68-520 nm. The dispersion was examined with an optical microscope. It exhibited excellent particle integrity, free flocculation and agglomeration. The dispersion particles exhibited rapid Brownian motion.

BIOAVAILABILITY TESTING

Bioavailability of Steroid A from the nanoparticulate dispersion described above was compared to that from a suspension of unmilled Steroid A (having an average particle size of about 100 μm) in male beagle dogs. The unmilled material was prepared as a suspension in the same manner as the dispersion, with the exception of the ball milling process. Both formulations were administered to each of five dogs by oral gavage and plasma obtained via a cannula in the cephalic vein. Plasma Steroid A levels were monitored over 24 hours. The relative bioavailability of Steroid A from the nanoparticulate dispersion was 7.1 fold higher than from the unmilled Steroid A suspension. Comparison of oral plasma levels with dose corrected plasma levels following intravenous administration of Steroid A gave a mean absolute bioavailability ($\pm$SEM) of 14.8$\pm$3.5% for the nanoparticulate dipersion and 2.1$\pm$1.0% for the unmilled material.

COMPARATIVE EXAMPLE A

A dispersion of Steroid A was prepared using a ball milling process with zirconium oxide grinding beads. The dispersion was prepared in the absence of a surface modifier and a post-sonication step was used to minimize flocculation and reaggregation.

A fine particle dispersion was prepared by ball milling the following ingredients:

5 g Steroid A
95 g high purity water

The following process conditions were used:

Grinding media: 135 ml
Vessel volume: 240 ml
Grinding media: 0.85-1.18 mm Zirbeads XR
Milling time: 4 days
Milling speed: 86 RPM (50% critical speed)

After four days of ball milling, the slurry was separated from the grinding media through a screen. One gram of the unstablized slurry was blended with 10 grams of high purity water and mixed by vigorous shaking, followed by a sonication step for 20 seconds using an ultrasonic horn (Model 350 Branson Ultrasonic Power Supply, Horn diameter=0.5 inch, Power setting=2). The slurry was sized under a microscope. An optical microscope equipped with phase contrast illumination was used to observe the condition of the dispersion.

A drop of the dilute slurry was placed between a microscope slide and a glass cover slip and observed at high magnification (400$\times$). The dispersion exhibited severe particle aggregation. The aggregate size was greater than 10 microns and exhibited no Brownian particle movement.

COMPARATIVE EXAMPLE B

Comparative Example A was repeated except that 1 gram of the slurry was added to 10 grams of a dilute solution (1% by weight) of PVP K-15. The resultant dispersion after 6 days was aggregated. The aggregate size was at least 5 microns. After 6 days of holding, the dispersion settled completely leaving a clear supernatant and a layer of Steroid A sediment.

COMPARATIVE EXAMPLE C

Comparative Example B was repeated except that the 1% PVP solution was replaced with a 1% solution of purified sodium methyl oleoyl taurate (available from GAF as Igepon T and subsequently purified at Eastman Kodak). After 6 days the dilute dispersion was partially flocculated and had many aggregates larger than 1 micron.

COMPARATIVE EXAMPLE D

Comparative Example B was repeated except that 1 gram of slurry was added to 10 grams of a 1% aqueous solution of polyethylene glycol (available from Union Carbide as PEG 3350). The dispersion after sonication was flocculated with particles larger than 35 microns.

COMPARATIVE EXAMPLE E

Comparative Example B was repeated except that the dispersion was diluted with an aqueous 1% solution of gum tragacanth (available from Eastman Kodak). This freshly prepared dispersion exhibited flocculation with particles 10 microns and larger.

COMPARATIVE EXAMPLE F

A dispersion of Danazol was prepared by ball milling with zirconium oxide grinding spheres. A cylindrical glass vessel was filled about halfway with the following ingredients:

Grinding media: 135 ml 0.85–1.18 mm Zirbeads XR
5 g Danazol
1 g PVP K-15
94 g high purity water This vessel was rotated horizontally on its axis at a controlled speed of 50% critical speed (85 RPM) for 4 days. The slurry was discharged and separated from the grinding media through a screen and examined for particle size with an optical microscope. The slurry was examined for particle size after holding it for 4 days at room temperature (23° C.). A drop of undiluted slurry was placed between a glass microscope slide and a glass cover slip and observed optically at high magnification (400X). The slurry was partially aggregated with particles up to 10 microns in diameter. Unlike Examples 1–5, the amount of PVP present was insufficient to hinder particle agglomeration.

The invention has been described in detail with particular reference to preferred embodiments thereof, but it will be understood that variations and modifications can be effected within the spirit and scope of the invention.

What is claimed is:

1. Particles consisting essentially of 99.9–10% by weight of a crystalline drug substance having a solubility in water of less than 10 mg/ml, said drug substance having a non-crosslinked surface modifier adsorbed on the surface thereof in an amount of 0.1–90% by weight and sufficient to maintain an effective average particle size of less than about 400 nm.

2. The particles of claim 1 having an effective average particle size of less than 250 nm.

3. The particles of claim 1 having an effective average particle size of less than 100 nm.

4. The particles of claim 1 wherein said drug substance is selected from analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, haemostatics, immuriological agents, lipid regulating agents, muscle relaxants, parasympathomimetics, parathyroid calcitonin, prostaglandins, radio-pharmaceuticals, sex hormones, anti-allergic agents, stimulants, sympathomimetics, thyroid agents, vasodilators and xanthines.

5. The particles of claim 1 wherein said drug substance is a steroid.

6. Particles consisting essentially of 99.9–10% by weight of a crystalline drug substance having a solubility in water of less than 10 mg/ml, said drug substance having a non-crosslinked surface modifier absorbed on the surface thereof in an amount of 0.1–90% by weight and sufficient to maintain an effective average particle size of less than about 400 nm, wherein said drug substance is selected from the group consisting of Danazol, $5\alpha,17\alpha,-1'$-(methylsulfonyl)-1'H-pregn-20-yno-[3,2-c]-pyrazol-17-ol, piposulfam, piposulfan, camptothecin, and ethyl-3,5-diacetamido-2,4,6-triiodobenzoate.

7. The particles of claim 1 wherein said surface modifier is selected from the group consisting of gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene caster oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone.

8. The particles of claim 1 wherein said surface modifier is selected from the group consisting of polyvinylpyrrolidone, an ethylene oxide-propylene oxide block copolymer, lecithin, an alkyl aryl polyether sulfonate, gum acacia, sodium dodecylsulfate, and a dioctylester of sodium sulfosuccinic acid.

9. Particles consisitng essentially of 80–40% by weight of crystalline danazol having polyvinyl pyrrolidone adsorbed on the surface thereof in an amount of 20–60% by weight and sufficient to maintain an effective average particle size of less than about 100 nm.

10. Particles consisting essentially of 99.9–10% by weight of crystalline $5\alpha, 17\alpha,-1'$-(methylsulfonyl)-1'H-pregn-20-yno-pyrazol-17-ol having an ethylene oxide propylene-oxide block copolymer adsorbed on the surface thereof in an amount of 0.1–90% by weight and sufficient to maintain an effective average particle size of less than about 400 nm.

11. A stable dispersion consisting essentially of a liquid dispersion medium and the particles of claim 1.

12. The dispersion of claim 11 wherein said dispersion medium is water.

13. The dispersion of claim 11 wherein said dispersion medium is selected from the group consisting of safflower oil, ethanol, t-butanol, hexane and glycol.

14. A pharmaceutical composition comprising the particles of claim 1 and a pharmaceutically acceptable carrier therefor.

15. A method of treating a mammal comprising the step of administering to the mammal an effective amount of the pharmaceutical composition of claim 14.

16. A method of preparing the particles of claim 1 comprising the steps of dispersing a drug substance in a liquid dispersion medium and wet grinding said drug substance in the presence of rigid grinding media having an average particle size of less than 3 mm and a surface modifier to reduce the particle size of said drug substance to an effective average particle size of less than about 400 nm.

17. A method of preparing the particles of claim 1 comprising the steps of dispersing a drug substance in a liquid dispersion medium, wet grinding said drug substance in the presence of rigid grinding media having an average particle size of less than 3 mm, thereafter contacting said drug substance with a surface modifier by mixing said surface modifier with said dispersion medium to form particles having an effective average particle size of less than about 400 nm.

18. The method of claim 17 further including the step of subjecting the dispersion medium containing said drug substance and said surface modifier to ultrasonic energy.

19. The method of claim 16 wherein said grinding media have an average particle size of less than 1 mm.

20. The method of claim 16 wherein said grinding media have a density greater than 3 g/cm$^3$.

* * * * *